US010775395B2

(12) United States Patent
Bittner et al.

(10) Patent No.: US 10,775,395 B2
(45) Date of Patent: Sep. 15, 2020

(54) SYSTEM AND METHOD OF PERFORMING A BIOLOGICAL EXPERIMENT WITH ADAPTIVE CYBERNETIC CONTROL OF PROCEDURAL CONDITIONS

(71) Applicant: Arctoris Limited, Oxford (GB)

(72) Inventors: Martin-Immanuel Bittner, Romsey (GB); Thomas Adam Fleming, Romsey (GB); Alice Poppy Roworth, Oxford (GB)

(73) Assignee: Arctoris Limited, Oxford (GB)

( * ) Notice: Subject to any disclaimer, the term of this patent is extended or adjusted under 35 U.S.C. 154(b) by 0 days.

(21) Appl. No.: 16/164,090

(22) Filed: Oct. 18, 2018

(65) Prior Publication Data

US 2020/0124626 A1 Apr. 23, 2020

(51) Int. Cl.
*G01N 35/00* (2006.01)

(52) U.S. Cl.
CPC ... *G01N 35/00613* (2013.01); *G01N 35/0099* (2013.01); *G01N 2035/00277* (2013.01)

(58) Field of Classification Search
None
See application file for complete search history.

(56) References Cited

U.S. PATENT DOCUMENTS

2006/0105359 A1* 5/2006 Favuzzi .................. B01L 3/508 435/6.19
2007/0048863 A1 3/2007 Rodgers et al.
(Continued)

FOREIGN PATENT DOCUMENTS

WO 2006/071716 A2 7/2006
WO 2016/161174 A1 10/2016
WO 2018/115161 A1 6/2018

OTHER PUBLICATIONS

International Search Report and Written Opinion from corresponding International Appl. No. PCT/IB2019/058739, dated Jan. 21, 2020.

(Continued)

*Primary Examiner* — Brian R Gordon
(74) *Attorney, Agent, or Firm* — Womble Bond Dickinson (US) LLP

(57) ABSTRACT

A method for performing a biological experiment includes accessing a protocol that specifies operations and prescribes a plurality of conditions for carrying out the biological experiment in a defined space. The method includes performing the sequence of operations according to the protocol; and periodically before or as the sequence of operations are performed, obtaining observations of particular conditions of the plurality, and comparing the particular conditions as observed to the particular conditions as prescribed. When a particular condition as observed deviates from the as prescribed by more than a predetermined threshold for the particular condition, the method includes interrupting the sequence of operations, accessing a corrective protocol that specifies an operation for remediating the particular condition as observed to within the predetermined threshold of the particular condition as prescribed, performing the operation to remediate the particular condition according to the corrective protocol, and resuming the sequence of operations.

15 Claims, 4 Drawing Sheets

(56) References Cited

U.S. PATENT DOCUMENTS

| | | | | |
|---|---|---|---|---|
| 2009/0298129 | A1* | 12/2009 | Spence | B01L 3/5085<br>435/91.2 |
| 2015/0278625 | A1* | 10/2015 | Finkbeiner | G02B 27/32<br>348/79 |
| 2017/0022558 | A1* | 1/2017 | Banyai | G01N 35/0092 |
| 2017/0335271 | A1* | 11/2017 | Maggiore | B33Y 30/00 |
| 2019/0002814 | A1* | 1/2019 | Masquelier | C12N 9/22 |
| 2019/0100721 | A1* | 4/2019 | Bernate | C12N 15/70 |
| 2019/0242916 | A1* | 8/2019 | Guarracina | B25J 9/1679 |
| 2020/0002662 | A1* | 1/2020 | Jaffray | G16H 20/40 |
| 2020/0049723 | A1* | 2/2020 | La Barrie | G01N 35/00623 |

OTHER PUBLICATIONS

Volkmer et al., "Overcoming Hypoxia in 3D Culture Systems for Tissue Engineering of Bone in vitro Using an Automated, Oxygen-Triggered Feedback Loop," Journal of Materials Science: Materials in Medicine, vol. 23, Jul. 2012, pp. 2793-2801.

* cited by examiner

SYSTEM AND METHOD OF PERFORMING A BIOLOGICAL EXPERIMENT WITH ADAPTIVE CYBERNETIC CONTROL OF PROCEDURAL CONDITIONS

TECHNOLOGICAL FIELD

The present disclosure relates generally to biological experimentation and, in particular, to biological experimentation with adaptive cybernetic control of procedural conditions.

BACKGROUND

Biomedical research encompasses a wide range of fields. Today, one of the most important is the study of cellular and molecular biology and diseases that originate at the cellular and molecular level.

Experiments in cellular and molecular biology can often be characterized as a sequence of steps beginning with preparation of a culture of a specific cell type in a suitable growth medium. Portions of the cell culture and growth medium are then dispensed into experimental containers (e.g., flask, test tube, or well plate), allowed to grow for some period of time (perhaps in an incubator, bioreactor or fermentor), the condition of the cell culture is observed or measured (e.g., microphotograph or cell count) the cell culture is treated with a reagent (defined as any substance that is used in an experimental protocol) of interest, perhaps allowed to grow again, and then again observed or measured or subjected to further processing before being observed or measured. In some instances, an experiment may start from a cell extract such as proteins, nucleic acids, organelles or membranes, or from another substance which is then processed, observed and measured. Finally, the observations and measurements are compared and used to determine the effect of the protocol, treatment or reagent and to gather information on a biological, physical or chemical phenomenon.

The cells used for biomedical research are often cultured from established cell lines originating from deceased donors, but can also be cells taken from living humans or other species and cultured thereafter. The process of cell culture itself, i.e., how to ensure the survival, growth and proliferation of the cells follows principles well known to those skilled in the art.

Today, for the most part, such experiments are performed manually in academic, research, pharmaceutical, biotechnological and clinical facilities that vary widely in the available equipment, procedural conditions, and also in the experience and expertise of technicians and scientists conducting the experiments. Experiments performed in limited facilities may be performed with great care but vary in outcome because of variation in temperature, humidity, pH, sample volume, particle concentrations, gas concentrations, exposure to light, cross contamination from other experiments, viral and bacterial contamination from ambient air, and aerosol contamination from other experimental reagents and antimicrobials, and/or other factors.

Variations in procedural conditions thereby cause various biological effects. For example both temperature and pH change the activity of enzymes (normally consisting of proteins), which are at the core of almost every biological process. In addition, genes can be expressed more or less strongly depending on e.g., oxygen levels or temperature. And these changes in gene expression levels can then in turn cause widespread changes in cell behavior, metabolism etc. These changes in turn have a significant impact on general cellular processes, but also on the effect of drugs or other experimental treatments on a cell.

BRIEF SUMMARY

Example implementations of the present disclosure are directed to performing a biological experiment as defined in an experiment protocol and, specifically, to the maintenance of protocol quality by the adaptive control of laboratory conditions. According to example implementations, this is achieved by monitoring laboratory conditions, detecting deviations from prescribed conditions and, when appropriate, performing a predetermined corrective protocol followed by resumption of the current experiment protocol. The capabilities afforded by example implementations underpin the high standards and quality control required by biomedical research, (bio-) pharmaceutical and cell and production, as well as cell and gene therapy.

The present disclosure thus includes, without limitation, the following example implementations.

Some example implementations provide a method of performing a biological experiment, the method comprising accessing a protocol for a biological experiment that specifies a sequence of operations and prescribes a plurality of conditions for carrying out a biological experiment in a defined space, the protocol being associated with corrective protocols for particular conditions of the plurality of conditions, the corrective protocols specifying operations for remediating respective ones of the particular conditions when the particular conditions as observed during the biological experiment deviate from the particular conditions as prescribed; performing the sequence of operations to carry out the biological experiment in the defined space according to the protocol, the sequence of operations including dispensing cells into a container with a growth medium, and transferring the container with the cells and the growth medium into an enclosure for culturing the cells; and periodically before or as the sequence of operations are performed, obtaining observations of the particular conditions at least some of which include an incubation period in which the container with the cells and the growth medium is held in the enclosure, physical and chemical conditions in the defined space or within the enclosure, one or more physical or chemical properties of the cells or the growth medium within the container, or conditions of the cells or their concentration within the container; and comparing the particular conditions as observed to the particular conditions as prescribed; and when a particular condition of the particular conditions as observed deviates from the particular condition as prescribed by more than a predetermined threshold for the particular condition, interrupting the sequence of operations; accessing a corrective protocol of the corrective protocols that specifies an operation for remediating the particular condition as observed to within the predetermined threshold of the particular condition as prescribed; performing the operation to remediate the particular condition according to the corrective protocol; and resuming the sequence of operations.

In some example implementations of the method of any preceding example implementation, or any combination of any preceding example implementations, when the particular condition as observed deviates from the particular condition as prescribed by less than a predetermined threshold for the particular condition, the method further comprises continuing the biological experiment without interrupting the sequence of operations to remediate the particular condition as observed.

In some example implementations of the method of any preceding example implementation, or any combination of any preceding example implementations, when the particular condition as observed deviates from the particular condition as prescribed by more than a critical threshold that is greater than a predetermined threshold for the particular condition, the method further comprises terminating the biological experiment without completing the biological experiment, and without remediating the particular condition as observed to within the predetermined threshold of the particular condition as prescribed.

In some example implementations of the method of any preceding example implementation, or any combination of any preceding example implementations, when a second particular condition of the particular conditions as observed deviates from the second particular condition as prescribed by less than a second predetermined threshold for the second particular condition, the method further comprises continuing the biological experiment without interrupting the sequence of operations to remediate the second particular condition as observed.

In some example implementations of the method of any preceding example implementation, or any combination of any preceding example implementations, when a second particular condition of the particular conditions as observed deviates from the second particular condition as prescribed by more than a second critical threshold that is greater than a second predetermined threshold for the second particular condition, the method further comprises terminating the biological experiment without completing the biological experiment, and without remediating the second particular condition as observed to within the second predetermined threshold of the second particular condition as prescribed.

In some example implementations of the method of any preceding example implementation, or any combination of any preceding example implementations, the particular conditions include the physical and chemical conditions in the defined space or within the enclosure, including temperature, humidity, and concentration of a gas in the defined space or within the enclosure.

In some example implementations of the method of any preceding example implementation, or any combination of any preceding example implementations, the particular conditions include the physical and chemical conditions in the defined space, including visible or ultraviolet light in the defined space.

In some example implementations of the method of any preceding example implementation, or any combination of any preceding example implementations, the particular conditions include the one or more physical or chemical properties of the cells or the growth medium, including temperature or pH of the growth medium.

In some example implementations of the method of any preceding example implementation, or any combination of any preceding example implementations, the particular conditions include the one or more physical or chemical properties of the cells or the growth medium, including a rate of freezing or thawing of the cells.

In some example implementations of the method of any preceding example implementation, or any combination of any preceding example implementations, the particular conditions include the conditions of the cells or their concentration within the container, including an appearance, size or shape of the cells, clusters of the cells or fragments thereof.

In some example implementations of the method of any preceding example implementation, or any combination of any preceding example implementations, the particular conditions include the conditions of the cells or their concentration within the container, including a quantified gene activity in the cells.

In some example implementations of the method of any preceding example implementation, or any combination of any preceding example implementations, the particular conditions include the conditions of the cells or their concentration within the container, including a count of adherent or floating cells, or confluence of the cells.

In some example implementations of the method of any preceding example implementation, or any combination of any preceding example implementations, the sequence of operations further includes adding a dye to the cells, and the particular conditions include the conditions of the cells or their concentration within the container, including a proportion of the cells to which the dye has attached, or an intensity with which the dye has attached to the cells or a proportion thereof.

In some example implementations of the method of any preceding example implementation, or any combination of any preceding example implementations, the method is performed in a laboratory with automated equipment including processing circuitry coupled to at least one robot and sensors, at least some of which are located in the defined space, wherein the protocol is machine-readable and accessed by the processing circuitry from a computer-readable storage medium, and the sequence of operations is performed by the automated equipment including the at least one robot under control of the processing circuitry, and wherein the observations are obtained by the processing circuitry from the sensors, and the processing circuitry compares the particular conditions, and when the particular condition as observed deviates from the particular condition as prescribed, the processing circuitry interrupts the sequence of operations, and accesses the corrective protocol from the computer-readable storage medium, the automated equipment performs the operation under control of the processing circuitry, and the processing circuitry resumes the sequence of operations.

Some example implementations provide a system for performing a biological experiment, the system comprising a computer-readable storage medium configured to store a protocol for a biological experiment that specifies a sequence of operations and prescribes a plurality of conditions for carrying out a biological experiment in a defined space, the protocol being associated with corrective protocols for particular conditions of the plurality of conditions, the corrective protocols specifying operations for remediating respective ones of the particular conditions when the particular conditions as observed during the biological experiment deviate from the particular conditions as prescribed; and automated equipment including processing circuitry coupled to at least one robot and sensors, at least some of which are located in the defined space, the processing circuitry configured to access the protocol from the computer-readable storage medium, wherein the automated equipment is configured to perform the sequence of operations under control of the processing circuitry to carry out the biological experiment according to the protocol, the sequence of operations including the at least one robot configured to dispense cells into a container with a growth medium, and transfer the container with the cells and the growth medium into an enclosure for culturing the cells; and periodically and automatically before or as the sequence of operations are performed, the sensors are configured to measure and thereby produce measurements of the particular conditions at least some of which include an incubation period in which the container with the cells and the growth medium is held in the enclosure, physical and chemical conditions in the defined space or within the enclosure, one or more physical or chemical properties of the cells or the growth medium within the container, or conditions of the cells or their concentration within the container, and the processing circuitry is configured to obtain the measurements and thereby observations of the particular conditions from the sensors; and the processing circuitry is configured to compare the particular conditions as observed to the particular conditions as prescribed; and when a particular condition of the particular conditions as observed deviates from the particular condition as prescribed by more than a predetermined threshold for the particular condition, the processing circuitry is configured to interrupt the sequence of operations, and access, from the computer-readable storage medium, a corrective protocol of the corrective protocols that specifies an operation for remediating the particular condition as observed to within the predetermined threshold of the particular condition as prescribed; the automated equipment is configured to perform the operation under control of the processing circuitry to remediate the particular condition according to the corrective protocol; and the processing circuitry is configured to resume the sequence of operations.

In some example implementations of the system of any preceding example implementation, or any combination of any preceding example implementations, when the particular condition as observed deviates from the particular condition as prescribed by less than a predetermined threshold for the particular condition, the processing circuitry is further configured to continue the biological experiment without the sequence of operations being interrupted to remediate the particular condition as observed.

In some example implementations of the system of any preceding example implementation, or any combination of any preceding example implementations, when the particular condition as observed deviates from the particular condition as prescribed by more than a critical threshold that is greater than a predetermined threshold for the particular condition, the processing circuitry is further configured to terminate the biological experiment without the biological experiment being completed, and without the particular condition as observed being remediated to within the predetermined threshold of the particular condition as prescribed.

In some example implementations of the system of any preceding example implementation, or any combination of any preceding example implementations, when a second particular condition of the particular conditions as observed deviates from the second particular condition as prescribed by less than a second predetermined threshold for the second particular condition, the processing circuitry is further configured to continue the biological experiment without the sequence of operations being interrupted to remediate the second particular condition as observed.

In some example implementations of the system of any preceding example implementation, or any combination of any preceding example implementations, when a second particular condition of the particular conditions as observed deviates from the second particular condition as prescribed by more than a second critical threshold that is greater than a second predetermined threshold for the second particular condition, the processing circuitry is further configured to terminate the biological experiment without the biological experiment being completed, and without the second particular condition as observed being remediated to within the second predetermined threshold of the second particular condition as prescribed.

In some example implementations of the system of any preceding example implementation, or any combination of any preceding example implementations, the particular conditions include the physical and chemical conditions in the defined space or within the enclosure, including temperature, humidity, and concentration of a gas in the defined space or within the enclosure.

In some example implementations of the system of any preceding example implementation, or any combination of any preceding example implementations, the particular conditions include the physical and chemical conditions in the defined space, including visible or ultraviolet light in the defined space.

In some example implementations of the system of any preceding example implementation, or any combination of any preceding example implementations, the particular conditions include the one or more physical or chemical properties of the cells or the growth medium, including temperature or pH of the growth medium.

In some example implementations of the system of any preceding example implementation, or any combination of any preceding example implementations, the particular conditions include the one or more physical or chemical properties of the cells or the growth medium, including a rate of freezing or thawing of the cells.

In some example implementations of the system of any preceding example implementation, or any combination of any preceding example implementations, the particular conditions include the conditions of the cells or their concentration within the container, including an appearance, size or shape of the cells, clusters of the cells or fragments thereof.

In some example implementations of the system of any preceding example implementation, or any combination of any preceding example implementations, the particular conditions include the conditions of the cells or their concentration within the container, including a quantified gene activity in the cells.

In some example implementations of the system of any preceding example implementation, or any combination of any preceding example implementations, the particular conditions include the conditions of the cells or their concentration within the container, including a count of adherent or floating cells, or confluence of the cells.

In some example implementations of the system of any preceding example implementation, or any combination of any preceding example implementations, the sequence of operations further includes the at least one robot being configured to add a dye to the cells, and the particular conditions include the conditions of the cells or their concentration within the container, including a proportion of the cells to which the dye has attached, or an intensity with which the dye has attached to the cells or a proportion thereof.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE FIGURE(S)

Having thus described example implementations of the disclosure in general terms, reference will now be made to the accompanying figures, which are not necessarily drawn to scale, and wherein:

DETAILED DESCRIPTION

Figure 1:
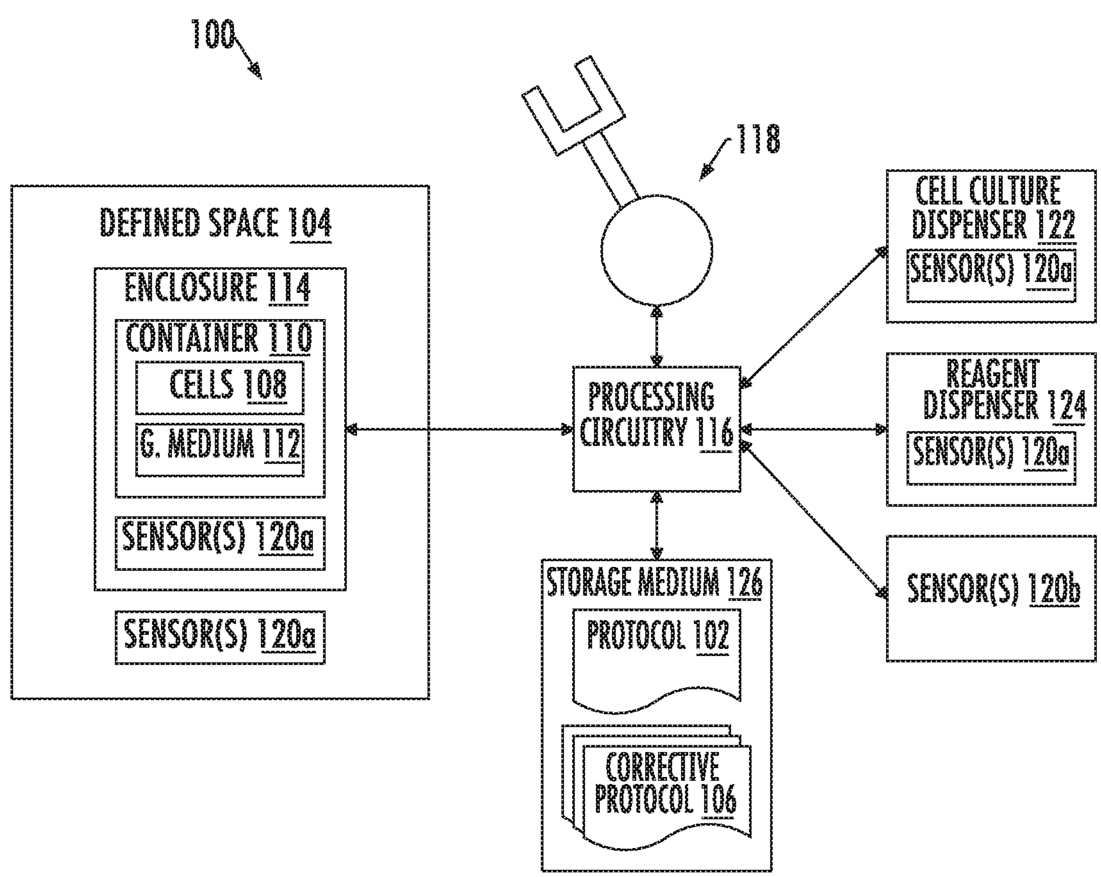
FIG. 1 illustrates a laboratory in which a biological experiment may be carried out, according to example implementations of the present disclosure.

Some implementations of the present disclosure will now be described more fully hereinafter with reference to the accompanying figures, in which some, but not all implementations of the disclosure are shown. Indeed, various implementations of the disclosure may be expressed in many different forms and should not be construed as limited to the implementations set forth herein; rather, these example implementations are provided so that this disclosure will be thorough and complete, and will fully convey the scope of the disclosure to those skilled in the art. As used herein, the term "and/or" and the "/" symbol includes any and all combinations of one or more of the associated listed items. Also, for example, reference may be made herein to quantitative measures, values, relationships or the like. Unless otherwise stated, any one or more if not all of these may be absolute or approximate to account for acceptable variations that may occur, such as those due to engineering tolerances or the like.

Further, unless otherwise indicated, something being described as being a first, second or the like should not be construed to imply a particular order. It should be understood that the terms first, second, etc. may be used herein to describe various steps, calculations, positions and/or the like, these steps, calculations or positions should not be limited to these terms. These terms are only used to distinguish one operation, calculation, or position from another. For example, a first position may be termed a second position, and, similarly, a second step may be termed a first step, without departing from the scope of this disclosure. Additionally, something may be described as being above something else (unless otherwise indicated) may instead be below, and vice versa; and similarly, something described as being to the left of something else may instead be to the right, and vice versa. As used in the specification, and in the appended claims, the singular forms "a," "an," "the," include plural referents unless the context clearly dictates otherwise. Like reference numerals refer to like elements throughout.

Example implementations of the present disclosure are directed to a system and method of performing a biological experiment that monitors, controls and compensates for deviations in conditions prescribed for the experiment. These experiments generally include a predetermined sequence of operations where each operation has a specific purpose. The purpose of some may be to dispense growth medium and living cells into experimental containers, while the purpose of others may be to introduce reagents that affect the living cells. Some operations simply serve to give the living cells time to grow and multiply, while other operations serve to measure or observe some aspect (condition) of the cells and cell culture.

The outcome of experiments in cellular and molecular biology may be substantially determined by the cumulative effects of the individual operations. At the same time, the outcome of an individual operation may be substantially affected by ambient conditions including temperature, humidity, and concentrations of $O_2$ and $CO_2$ in the vicinity of the experiment. The outcome may also be substantially affected by pH, salinity, and concentrations of nutrients and reagents within the experimental containers, and the physical condition of the cells and their concentration within the growth medium.

To be of value, experiments in cellular and molecular biology must often yield similar results when repeated. Otherwise, there is no way assure that the outcome of an experiment is directly related to the predetermined sequence of operations and no way to assure that new results obtained when one or more operations are changed are directly related to the changes. In practice, variance in the outcome of laboratory experiments may be largely attributed to deviations in conditions such as those above. Example implementations of the present disclosure therefore provide a system and method to substantially reduce these deviations by monitoring, controlling, and compensating for them when they occur.

FIG. 1 illustrates a laboratory 100 in which a biological experiment may be performed according to example implementations of the present disclosure. As described herein, the biological experiment may be any of a number of different experiments such as a cellular or molecular biology experiment, process or medical course of action, such as in cell and gene therapy, or the like. As shown, a protocol 102 for the biological experiment specifies a sequence of operations and prescribes a plurality of conditions for carrying out the biological experiment in a defined space 104. Suitable experiments often include dispensing one more samples of a cell culture into one or more containers, adding a growth medium that may include a nutrient liquid that sustains the living cells and a reagent that affects some aspect of cell metabolism or genetic expression, incubate for some period of time to allow the effects to take place, and measure the effects.

In some more particular examples, the protocol 102 is a human and/or machine-readable specification of the sequence of operations and plurality of conditions, along with technical and scientific specifications of the conduct of each individual operation and combination of operations. This may include their timing, sequence, start and end, repetition, input, output, required devices (e.g., liquid handling stations, light measurement, microscopes, robotic transfer). Some examples of suitable conditions include in situ conditions such as procedural conditions and analytical conditions that can be observed or measured before or as the sequence of operations are performed to carry out the biological experiment. Procedural conditions are those that, when they fall outside what is prescribed, may affect the outcome of the experiment, such as temperature, humidity, pH, sample volume, particle concentrations, gas (e.g., $O_2$, $CO_2$) concentrations, exposure to light, and others. Analytical conditions are those that contain information on the effects of an experimental protocol on a sample, such as cell number, morphological features, color changes, movement, size, and others.

The success of the experiment may depend upon faithful performance of the sequence of operations maintaining the prescribed conditions during the course of the experiment, or successfully correcting those conditions and their effects when deviations are detected. The protocol 102 may therefore be represented as a sequence of operations and prescribed conditions (the prescribed at times being considered nominal), where each operation includes at least one task and may include required local conditions, calculations, etc.

The defined space 104 may be different for different laboratories or experiments. In some examples, the defined space is simply a room or a workbench therein. In other examples, the defined space is an environmentally-controlled laboratory hood or enclosed workstation within a room, and that may but need not contain laboratory equipment used in performing the experiment.

According to example implementations of the present disclosure, the protocol 102 is associated with corrective protocols 106 for particular conditions of the plurality of conditions. In this regard, the corrective protocols specify operations for remediating respective ones of the particular conditions when the particular conditions as observed during the biological experiment deviate from the particular conditions as prescribed. In some examples, the particular conditions may include some but not all of the plurality of conditions specified by the protocol (e.g., key conditions). In other examples, the particular conditions include all of the plurality of conditions.

In practice, the sequence of operations may be performed to carry out the biological experiment in the defined space 104 according to the protocol 102. As suggested above, the sequence of operations include dispensing cells 108 into a container 110 with a growth medium 112, and transferring the container with the cells and the growth medium into an enclosure 114 for culturing the cells. A sample may refer to any part or aliquot of a substance, reagent or cell used in an experiment as well as to the material outcome of any experiment; this may include for example treated or untreated cells, specific reagents, cellular extracts, proteins, nucleic acids, amplified oligonucleotides, dyed cells or any combinations of any of these. Examples of suitable containers include SBS-format well plates, flasks, vials, tubes, imaging plates, microscope slides, bottles, boxes and the like. And one example of a suitable enclosure is an incubator, although other enclosures that may not qualify as an incubator may be used in certain experiments.

Periodically before or as the sequence of operations are performed, at least the particular conditions for which there are corrective protocols are monitored and remediated when appropriate. These particular conditions may include an incubation period in which the container with the cells and the growth medium is held in the enclosure, physical and chemical conditions in the defined space or within the enclosure, one or more physical or chemical properties of the cells or the growth medium within the container, or conditions of the cells or their concentration within the container.

More particularly, periodically, observations of the particular conditions may be obtained, and the particular conditions as observed are compared to the particular conditions as prescribed. As explained in greater detail below, in some examples, these observations are measurements from sensors within the laboratory 100 either inside or outside the defined space 104, depending on the experiment and particular condition. When a particular condition of the particular conditions as observed deviates from the particular condition as prescribed by more than a predetermined threshold for the particular condition, the sequence of operations may be interrupted and a corrective protocol of the corrective protocols 106 may be accessed to remediate the particular condition. This corrective protocol in particular may specify an operation for remediating the particular condition as observed to within the predetermined threshold of the particular condition as prescribed. The operation may then be performed to remediate the particular condition according to the corrective protocol, and the sequence of operations may be resumed.

According to the above, the particular condition may therefore be remediated when its observed deviates from what is prescribed by more than a predetermined threshold for the particular condition. In other cases in which the observed deviates by less than the predetermined threshold, the biological experiment may continue without interruption and remediation. That is, in some examples, the biological experiment may continue without interrupting the sequence of operations to remediate the particular condition as observed, when the particular condition as observed deviates from the particular condition as prescribed by less than a predetermined threshold for the particular condition. Similarly, in some examples, the biological experiment may continue without interrupting the sequence of operations to remediate a second particular condition as observed, when the second particular condition as observed deviates from the second particular condition as prescribed by less than a second predetermined threshold for the second particular condition.

In yet other cases in which the observed deviates by more than a critical threshold, the biological experiment may terminate without being completed. In some examples, then, the particular condition as observed deviates from the particular condition as prescribed by more than a critical threshold that is greater than a predetermined threshold for the particular condition. In these examples, the biological experiment may terminate without it being completed, and without remediating the particular condition as observed to within the predetermined threshold of the particular condition as prescribed. Likewise, in some examples, a second particular condition as observed deviates from the second particular condition as prescribed by more than a second critical threshold that is greater than a second predetermined threshold for the second particular condition. In these examples, the biological experiment may terminate without it being completed, and without remediating the second particular condition as observed to within the second predetermined threshold of the second particular condition as prescribed.

Again, the particular conditions that may be monitored and remediated include, for example, an incubation period in which the container 110 with the cells 108 and the growth medium 112 is held in the enclosure 114, physical and chemical conditions in the defined space 104 or within the enclosure, one or more physical or chemical properties of the cells or the growth medium within the container, or conditions of the cells or their concentration within the container. More particular examples of physical and chemical conditions in the defined space or within the enclosure include temperature, humidity, and concentration of a gas in the defined space or within the enclosure. Additional examples of physical and chemical conditions in the defined space include visible or ultraviolet light in the defined space.

Examples of physical or chemical properties of the cells 108 or the growth medium 112 include temperature or pH of the growth medium. Other examples include a rate of freezing or thawing of the cells.

Examples of conditions of the cells 108 or their concentration within the container 110 include an appearance, size or shape of the cells, clusters of the cells or fragments thereof. Other examples include a quantified gene activity in the cells such as gene silencing, amplification, augmentation or the like, which may be measured, for example, by RNA (ribonucleic acid) or protein quantification using techniques such as qPCR (quantitative polymerase chain reaction), Western blotting or the like. Yet other examples include a count of adherent or floating cells, or confluence of the cells. And in some examples in which the sequence of operations of the protocol 102 further includes adding a dye to the cells, conditions of the cells or their concentration within the container may include a proportion of the cells to which the dye has attached, or an intensity with which the dye has attached to the cells or a proportion thereof.

The laboratory 100 may be equipped to perform the biological experiment manually. Or the laboratory may include automated equipment, at least some of which is located in the defined space 104, for automated or semi-automated performance of the experiment, as well as periodic and automatic monitoring and remediation of particular conditions. In some examples, this automated equipment includes the enclosure 114, such as when the enclosure is an automated incubator. As also shown in FIG. 1, this automated equipment may include processing circuitry 116 coupled to at least one robot 118 and sensors 120, and that may also be coupled to the enclosure. Also shown is an automated cell culture dispenser 122 and an automated reagent dispenser 124, either or both of which may be specifically equipped with one or more of the robot(s).

The processing circuitry 116 may be composed of one or more processors alone or in combination with one or more memories. The processing circuitry is generally any piece of computer hardware that is capable of processing information such as, for example, data, computer programs and/or other suitable electronic information, including machine-readable versions of the protocol 102 and corrective protocols 106. The processing circuitry is composed of a collection of electronic circuits some of which may be packaged as an integrated circuit or multiple interconnected integrated circuits (an integrated circuit at times more commonly referred to as a "chip"). The processing circuitry may be configured to execute computer programs, which may be stored onboard the processing circuitry or otherwise stored in memory (of the same or another apparatus).

The processing circuitry 116 may be a number of processors, a multi-core processor or some other type of processor, depending on the particular implementation. Further, the processing circuitry may be implemented using a number of heterogeneous processor systems in which a main processor is present with one or more secondary processors on a single chip. As another illustrative example, the processing circuitry may be a symmetric multi-processor system containing multiple processors of the same type. In yet another example, the processing circuitry may be embodied as or otherwise include one or more ASICs, FPGAs or the like. Thus, although the processing circuitry may be capable of executing a computer program to perform one or more functions, the processing circuitry of various examples may be capable of performing one or more functions without the aid of a computer program. In either instance, the processing circuitry may be appropriately programmed to perform functions or operations according to example implementations of the present disclosure.

The robot(s) 118 may be any of a number of different machines configured to automatically carry out one or more actions, such as under control of the processing circuitry 116. Examples of suitable robots include those typically involved in laboratory robotics.

The sensors 120 include any of a number of different devices configured to detect events or changes in their environment and produce relevant information (e.g., observations, measurements), which may be sent to the processing circuitry. Examples of suitable sensors include procedural sensors 120*a*, analytical sensors 120*b* and the like. Procedural sensors are configured to measure procedural conditions, and may include biometric sensors, imaging systems, pH meters, devices for the quantification of gaseous components or particle concentrations, and the like. Analytical sensors are configured to measure analytical conditions, and may include biometric sensors, imaging systems, spectrophotometers, size-separation devices, mass spectrometers, microscopes, nucleic acids sequencers, and the like.

Figure 2:
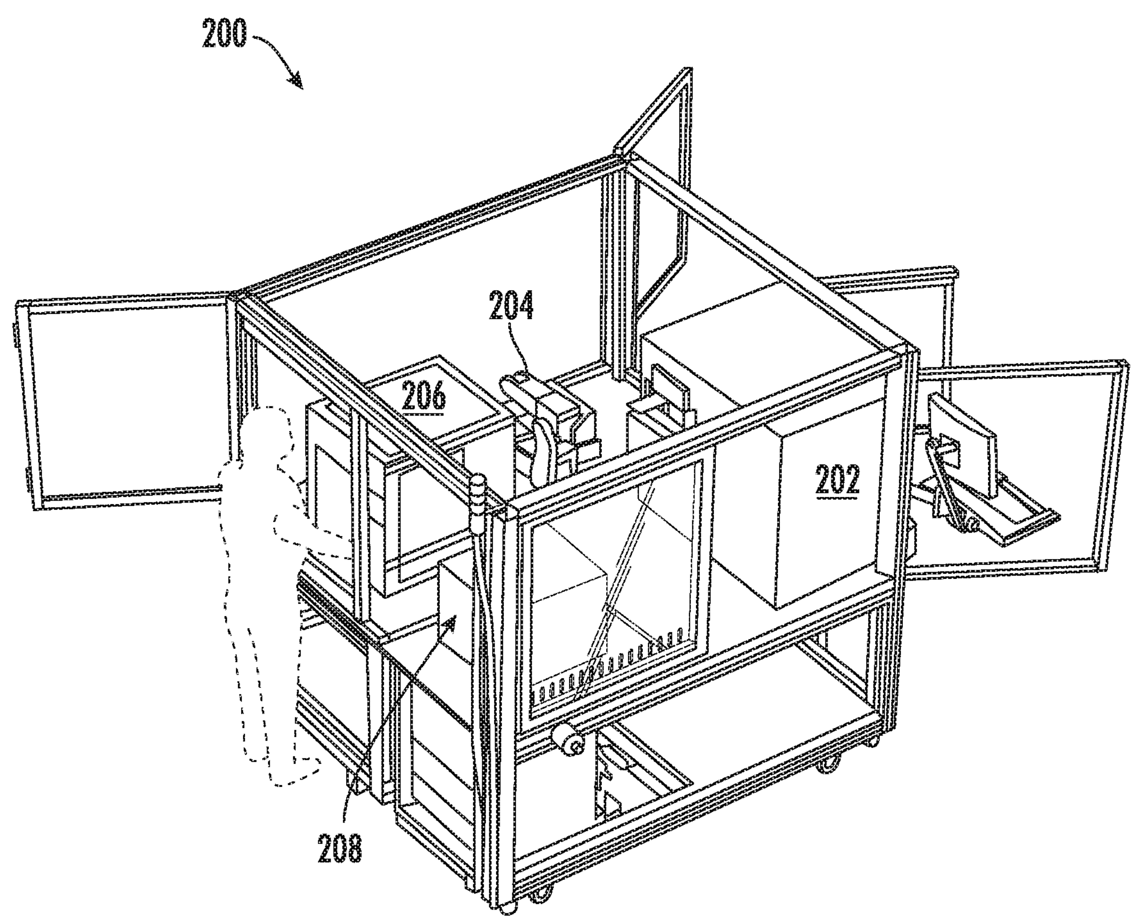
FIG. 2 illustrates an enclosed workstation that in some examples may correspond to a defined space in which a biological experiment may be carried out, according to some example implementations.

FIG. 2 illustrates an enclosed workstation 200 that in some examples may correspond to the defined space 104. As shown, the workstation includes an automated incubator 202 (enclosure 114) and a robotic arm 204 (robot 118). The workstation also includes a cell culture/reagent dispenser 206 (cell culture dispenser 122/reagent dispenser 124) that is itself equipped with a robot. The workstation further includes an analytical sensor 208 (analytical sensor 120*b*).

Figure 3:
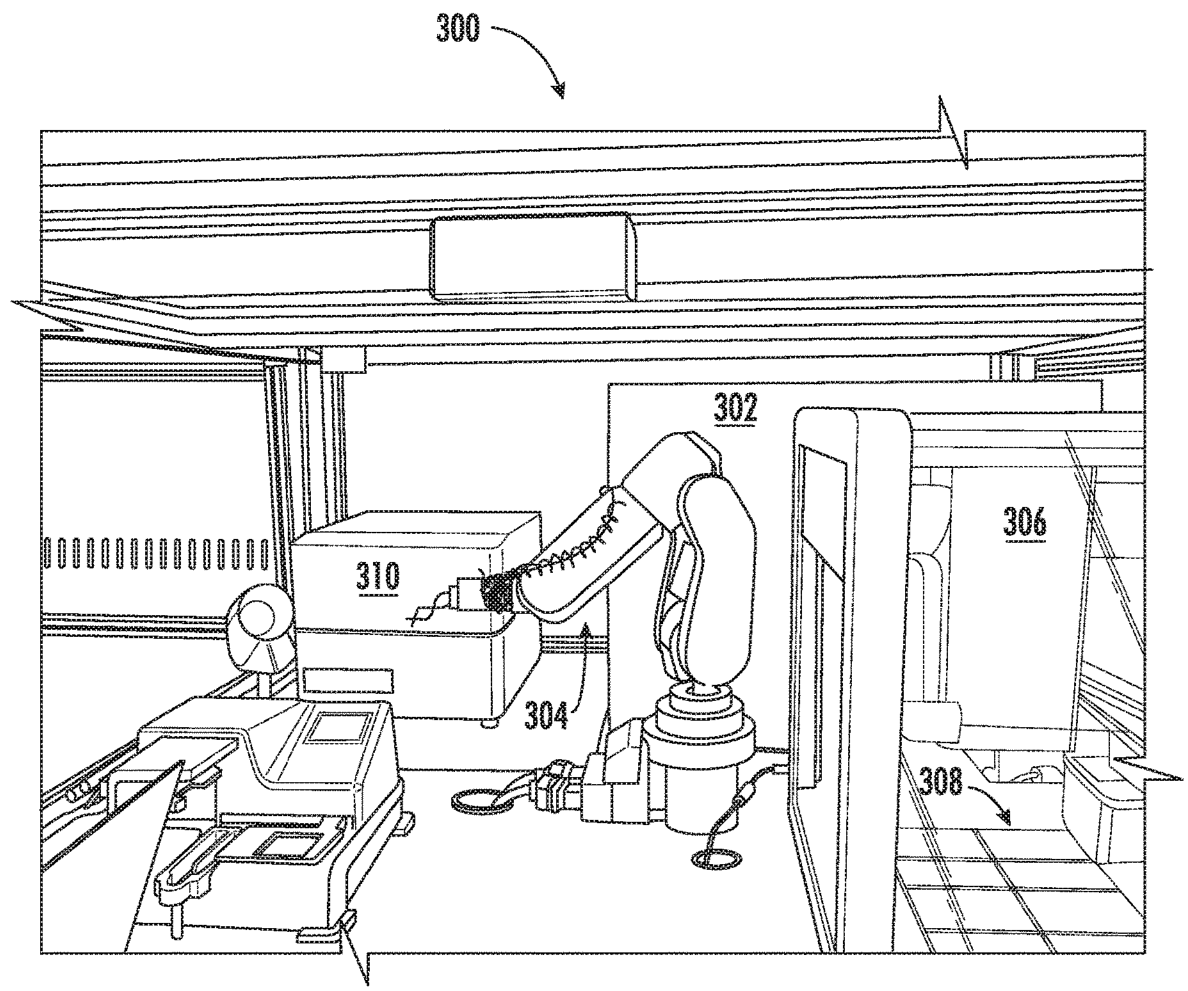
FIG. 3 illustrates a portion of laboratories with automated equipment, according to some example implementations.

FIG. 3 illustrates a portion of a laboratory 300 including automated equipment, according to some examples. As shown, this laboratory includes an automated incubator 302 (enclosure 114) and a robotic arm 304 (robot 118). The laboratory includes a cell culture/reagent dispenser 306 (cell culture dispenser 122/reagent dispenser 124) with experimental containers 308 (container 110), and that is itself equipped with a robot. The laboratory further includes an analytical sensor 310 (analytical sensor 120*b*).

Returning to FIG. 1, the protocol 102 and corrective protocols 106 may be human readable. But in some examples in which the laboratory 100 includes automated equipment, the protocol and corrective protocols may be machine-readable and accessed by the processing circuitry 116 from a computer-readable storage medium 126. In these examples, the sequence of operations of the protocol may be performed by the automated equipment including the robot (s) 118 under control of the processing circuitry. The processing circuitry may translate the protocol into messages, and send the messages to the automated equipment including in various examples the enclosure 114, robot(s), cell culture dispenser 122, reagent dispenser 124 and/or sensors 120, any one or more of which may include their own processing circuitry. The robot(s)—including any with which the cell culture dispenser is equipped—may thereby be configured to dispense cells 108 into the container 110 with the growth medium 112. And the robot(s) may be configured to transfer the container with the cells and the growth medium into the enclosure 114 for culturing the cells, before or after which the robot(s) may add a reagent to the container from the reagent dispenser 124.

Periodically before or as the sequence of operations are performed, the processing circuitry 116 may be configured to obtain observations from the sensors 120, and compare the particular conditions. When the particular condition as observed deviates from the particular condition as prescribed, the processing circuitry may be configured to interrupt the sequence of operations, and access the corrective protocol 106 from the computer-readable storage medium 126. The automated equipment may be configured to perform the operation specified by the corrective protocol under control of the processing circuitry, and the processing circuitry may be configured to then resume the sequence of operations.

Figure 4:
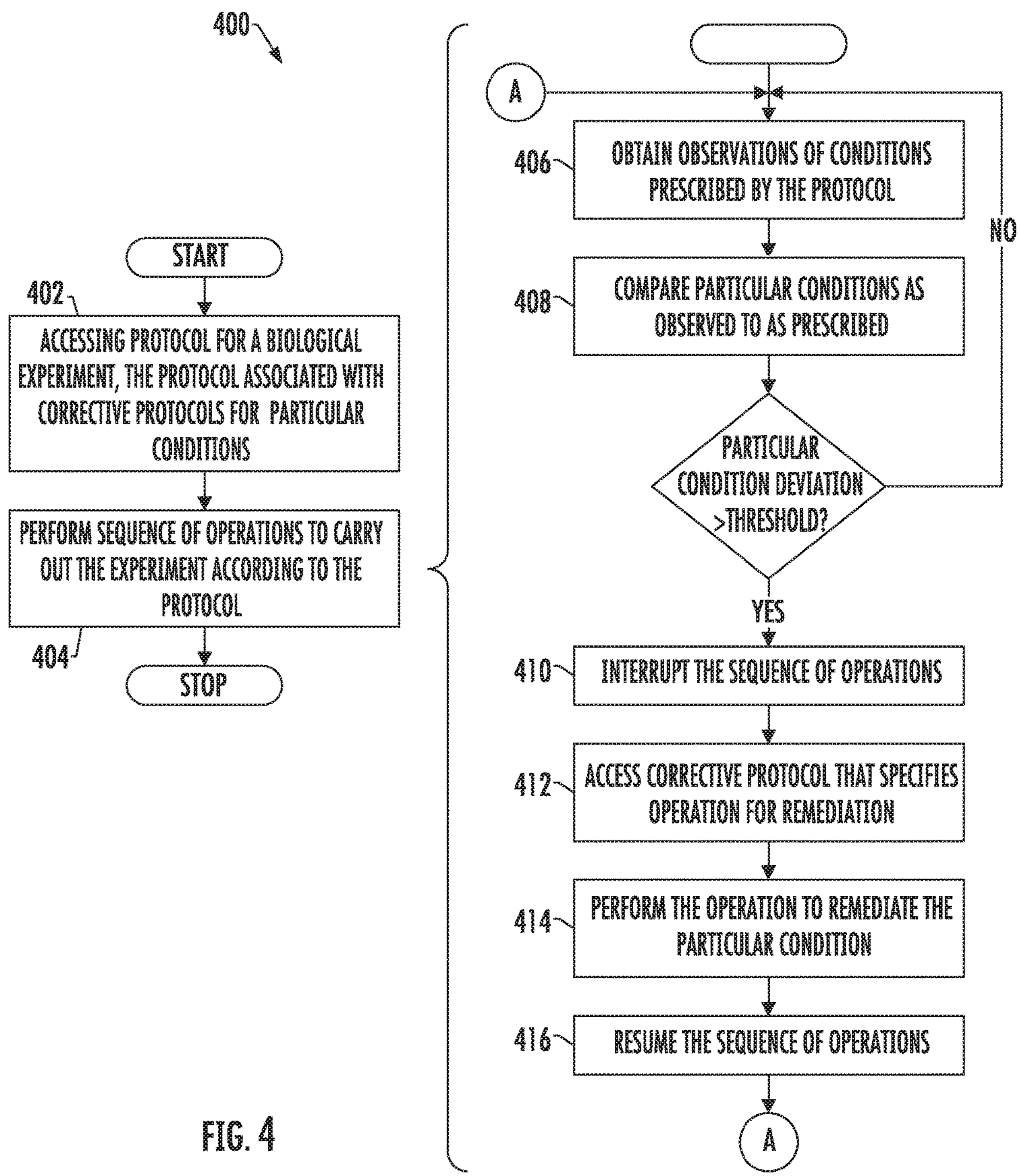
FIG. 4 is a flowchart illustrating various steps in a method of performing a biological experiment, according to example implementations.

FIG. 4 is a flowchart illustrating various steps in a method 400 of performing a biological experiment, according to example implementations of the present disclosure. As shown at block 402, the method includes accessing a protocol 102 for a biological experiment that specifies a sequence of operations and prescribes a plurality of conditions for carrying out the biological experiment in a defined space 104. The protocol is associated with corrective protocols 106 for particular conditions of the plurality of conditions, and the corrective protocols specify operations for remediating respective ones of the particular conditions when the particular conditions as observed during the biological experiment deviate from the particular conditions as prescribed.

The method includes performing the sequence of operations to carry out the biological experiment in the defined space 104 according to the protocol, as shown at block 404. The sequence of operations include dispensing cells 108 into a container 110 with a growth medium 112, and transferring the container with the cells and the growth medium into an enclosure 114 for culturing the cells. Periodically before or as the sequence of operations are performed, the method includes obtaining observations of the particular conditions, and comparing the particular conditions as observed to the particular conditions as prescribed, as shown at blocks 406 and 408.

When a particular condition of the particular conditions as observed deviates from the particular condition as prescribed by more than a predetermined threshold for the particular condition, the method includes interrupting the sequence of operations, as shown at block 410. The method also includes accessing a corrective protocol of the corrective protocols 106 that specifies an operation for remediating the particular condition as observed to within the predetermined threshold of the particular condition as prescribed, as shown at block 412. And the method includes performing the operation to remediate the particular condition according to the corrective protocol, and resuming the sequence of operations, as shown at blocks 414, 416.

To further illustrate example implementations of the present disclosure, consider that in general, factors that affect the outcome of individual operations and thereby affect the results of a biological experiment, including those in cellular and molecular biology, can be divided into two categories.

The first category includes physical and chemical conditions that can be measured and controlled by physical means including temperature, humidity, and concentrations of $O_2$ and $CO_2$ in the vicinity of the experiment, and pH and concentrations of nutrients, electrolytes and reagents within a container. In a first set of cases, deviation of the observed from the prescribed in one of these conditions can be immediately corrected, when discovered, by a physical change. For example, water can be added to the experimental container to compensate for liquid lost because of low humidity. In a second set of cases, deviation in one of these conditions may require a physical change followed by some duration of time for the change to have corrective effect. For example, the temperature in the vicinity of an experiment can be immediately raised, when discovered to be too low and thereby suppressing cell growth, but it may take some time for the cell culture to reach the target temperature and it may take some additional time for the cell culture to reach its growth target, with periodic inspection to determine when the growth target has been reached.

The second category is the observable condition of cells and their concentration within a growth medium. In a first set of cases for the second category, deviation in the observed condition of the cells and their concentration within the growth medium can be immediately corrected, when discovered, by a physical change. For example, liquid in the experimental container can be diluted if the concentration of cells is too high. In a second set of cases for the second category, deviation in the observed condition of the cells and their concentration within the growth medium may require a physical change followed by some duration of time for the change to have corrective effect. For example, the purpose of one operation may be to allow the cells to grow and multiply until they settle and adhere to the inner surface of the container. However, it may not be possible to precisely determine how long that may take. Giving the cells a fixed period of time to grow and then adhere (whether too long or too short), may leave the cells in a condition unsuitable for the following experimental operation. Instead, if inspection reveals slow growth, additional nutrients can be added to the cell culture, and additional time may be given for additional growth, with periodic inspection to determine when the target cell condition has been achieved.

It should be noted that allowing more time will often be a factor in compensating for deviations in laboratory conditions, but it may not always be possible to compensate for too much time already expended. And it should be noted that, in some examples, calculations may be performed to determine a compensating volume of water or growth medium to add, or duration of time for continued incubation.

In a more particular example, the protocol 102 for a biological experiment may specify the following sequence of five operations: (1) seed cancer cells (cells 108) in 96-well plates (containers 110) in an automated cell culture dispenser (dispenser 122), (2) incubate these cells in an automated incubator (enclosure 114) at 37° C., 5% $CO_2$ for 24 hours, (3) add three cancer drugs to the cells by an automated reagent dispenser (dispenser 124), (4) another incubation in the automated incubator at 37° C., 5% $CO_2$ for 24 hours, and (5) taking a readout in an analytical sensor (sensor 120*b*). Movement of the well plates between the various equipment may be conducted by a robot 118, under control of processing circuitry 116.

In some examples, the automated equipment performing the operations are in a defined space 104 large enough to contain the equipment, and designed to maintain stable ambient conditions, including the ability to modify certain conditions independently or in combination.

The defined space 104 may be equipped with procedural sensors 120*a* configured to precisely measure conditions as prescribed by the protocol 102 (e.g., temperature, $O_2$ and/or $CO_2$ concentration, humidity with an accuracy of 0.01-10% of prescribed values). The defined space may also be equipped with other devices (also generally sensors) that may be pertinent to controlling prescribed conditions, such as cameras and tracking devices configured to monitor the level of liquid in samples and the position and status of sample containers 110.

The processing circuitry 116 may be configured to execute the operations of the experiment in accordance with the protocol 102 and to record data acquired by the analytical and procedural sensors 120*a*, 120*b* to confirm that conditions are properly maintained. The processing circuitry may be configured to detect deviations between observed and prescribed conditions, and, if there is sufficient deviation, to execute corrective protocols 106 to keep or return conditions as observed within an acceptable deviation. The processing circuitry may also log any alterations and record deviations.

The following elaborates on a number of example conditions and corrective protocols 106 with operations that may be performed to remediate unacceptable deviations in those conditions.

Temperature Deviation, Lower than Prescribed

A deviation in the observed sample temperature from the prescribed sample temperature by −1° C. (degrees Celsius) may cause a reduction in the efficiency of a physical or chemical process. Examples include enzyme activity within a living cell, thereby altering metabolism, or in other experimental procedures such as during cDNA (complementary DNA) synthesis, or restriction enzyme DNA (deoxyribonucleic acid) digestion. Other examples include application of high pressure, or treatment with a substance. This may result in insufficient or reduced quantities of cell lysate extracted for downstream analysis.

In response to a detected deviation from the prescribed sample temperature, example implementations may alter a specific parameter or set of parameters by a specified amount in accordance with the predetermined corrective protocol 106 to return the experiment to its overall prescribed conditions. This may be implemented by the processing circuitry 116 which executes a corrective protocol that adjusts the duration of a process operation, for example, by extending an incubation period by 10% in response to a decrease in temperature by sending a command to the automated equipment (or their respective processing circuitry) to prolong the period of time the sample is held in a certain device.

This deviation may be detected by periodic (e.g., at a minimum of once per minute) measurement of temperature and when the temperature deviates from the prescribed by −1° C. below the prescribed or more, for more than 1 minute or more, the corrective procedure may be invoked.

This deviation may be remediated by first determining the magnitude of the deviation measured in degrees Celsius and by also determining the duration of the deviation measured in seconds. And then the subject of the experiment may be held in an incubator (enclosure 114) at prescribed temperature, for a duration of time determined by the magnitude and duration of the deviation.

Temperature Deviation, Higher than Prescribed

A deviation in the observed sample temperature from the prescribed sample temperature by +1° C. may cause an increase in the efficiency of a physical or chemical process such as enzyme activity within the cell, thereby altering metabolism. Alternatively, in other experimental procedures higher temperatures may degrade RNA or protein extracts, or denature them entirely at very high temperatures. Yet other examples include application of high pressure, or treatment with a substance. This may result in increased protein degradation in the cell lysate extracted for downstream analysis.

In response to a detected deviation from the prescribed sample temperature, example implementations may alter a specific parameter or set of parameters by a specified amount in accordance with the predetermined corrective protocol 106 to return the experiment to its overall prescribed conditions. This may be implemented by the processing circuitry 116 which executes a corrective protocol that adjusts the duration of a process operation, for example, by shortening an incubation period by 10% in response to an increase in temperature by sending a command to the automated equipment (or their respective processing circuitry) to shorten the period of time the sample is held in a certain device.

This deviation may be detected by periodic (e.g., at a minimum of once per minute) measurement of temperature and when the temperature deviates from the prescribed by +1° C. above the prescribed or more, for more than 1 minute or more, the corrective protocol may be invoked.

This deviation may be remediated by first determining the magnitude of the deviation measured in degrees centigrade and by also determining the duration of the deviation measured in seconds. And then the subject of the experiment may be held in an incubator at prescribed temperature, for a duration of time determined by the magnitude and duration of the deviation, or may be actively cooled to a certain temperature determined by substantially the same means.

pH Deviation, Higher or Lower than Prescribed

In another example, a deviation from the prescribed sample pH by 0.5 units may affect the viability and behavior of cultured biological cells or other experimental setups, such as those for chemical experiments, molecular experiments and the like.

In response to a detected deviation from the prescribed pH, the processing circuitry 116 may adapt the $O_2$ and $CO_2$ levels within the corresponding defined space 104, enclosure 114 or container 110 to return the experiment to their overall prescribed procedural conditions. In some examples, this may be accomplished by sending a command to an automated valve on a $O_2/CO_2$ container, releasing more or less $O_2/CO_2$. In another example of a corrective protocol 106 for a deviation from the prescribed pH, a substance may be added to the sample in the container to alter the pH of the sample (e.g., a certain acidic or basic substance empirically shown to correct for the deviation in pH).

Here, key conditions may include pH, environmental $O_2$ and $CO_2$, volume of liquid in individual experimental containers 110/compartments of an experimental container. The deviation may be detected by periodic sampling, with a sterile pipette, and using an appropriate sensor 120 to measure the pH. In the case of living cells 108, this condition may be detected by periodic (e.g., at a minimum of once per minute) measurement of $CO_2$. And when the $CO_2$ deviates from the prescribed by +/−2% from prescribed or more, for more than 10 minutes or more, the processing circuitry 116 may invoke the corrective protocol 106.

To remediate the deviation, the environmental $O_2$ and $CO_2$ may be increased or decreased, leading to a corresponding change in pH in case of living cells, testing every few minutes until the required pH is obtained. Alternatively, and in other types of samples, a specific volume of an acidic or basic substance of a specific pH determined by the volume of sample liquid, the actual sample pH, and the prescribed sample pH, may be added to the samples contained in the container 110.

Humidity Deviation, Higher or Lower than Prescribed

In yet another example applicable to a variety of experiments including cellular, chemical and molecular experiments, a deviation of 20% below the prescribed container humidity for 1 hour may affect the rate of evaporation, and thus the amount of liquids present in a sample or the container 110. Assuming there is 1,000 μL (microliters) in each sample-containing cavity of an experimental container, reducing the humidity by 20% below prescribed conditions for 1 hour may have concentrated the liquid remaining in the sample-containing cavities by 15%.

In response to such a detected deviation from the prescribed humidity, the processing circuitry 116 may adapt by adding a specified amount of liquid of a certain type to the samples or cavities in the container 110 by sending a command to the automated reagent dispenser 124 (or its processing circuitry) to return the experiment to their overall prescribed conditions, taking into account particle and reagent concentrations.

Key conditions may include measured temperature and humidity in the defined space 104 or enclosure 114, and volume, salinity and concentration of specific substances within the sample/liquid in the container 110 or its compartments. The deviation may be detected by periodic (e.g., at a minimum of once per minute) measurement of temperature and humidity of the environment, and when the temperature-corrected humidity deviates 10% or more above or below the prescribed, for 1 minute or more, an additional readout may be taken of the sample volume, salinity and concentration of specific substances pertaining to the experiment. When the processing circuitry 116 detects that any of these parameters deviates 10% or more above or below the prescribed parameters, the processing circuitry may invoke the appropriate corrective protocol 106.

Key conditions may include measured temperature and humidity in the defined space 104 or enclosure 114, and volume, salinity and concentration of specific substances within the sample/liquid in the container 110 or its compartments.

To remediate the deviation, the humidity in the defined space 104 or enclosure 114 may be increased or decreased by means of adding a composition of gases substantially similar to the composition already present in the defined space or enclosure, but with either an increased or decreased humidity. This may lead to a corresponding increase or decrease in humidity in the defined space or enclosure. In addition, a specific volume of a liquid substantially the same as the liquid already contained in the container 110 or its compartments kept in the defined space or enclosure may be added to the container or its compartments, with the amount determined by the volume of sample liquid, the salinity of the sample liquid, and the concentration of specific substances pertaining to the experiment.

Time Deviation, Higher than Prescribed

In yet another example applicable to a variety of experiments including cellular, chemical and molecular experiments, the duration of incubation of a sample with certain reagents can vary due to unforeseen circumstances, leading to a deviation from the prescribed timings or conditions of the respective experiment. A prolonged incubation with a substance (such as trypsin) by a certain time period (e.g., 10 minutes) can cause subsequent alterations in biological behavior, such as a prolonged time required for cells to complete their process of adherence to a container 110. In this case, an empirically-derived corrective protocol 106 may be initiated to account for this deviation, such as by prolonging the duration of a cell-adhesion operation, to revert the experiment to its overall prescribed course.

To detect this deviation, the time each sample spends in any given condition may be logged as part of the protocol 102. When the time has exceeded the prescribed time by a predetermined amount, the processing circuitry 116 may invoke the corrective protocol.

This deviation may be corrected by first determining the length of the deviation measured in seconds. And then the subject of the experiment may be prioritized within the schedule for immediate action of the next operation and downstream processing of the sample may be adjusted as determined by the magnitude and duration of the deviation.

UV Deviation, Higher or Lower than Prescribed

In yet another example applicable to a variety of experiments including cellular, chemical and molecular experiments, an increased amount of ultraviolet light (UV) exposure going beyond the prescribed range for a specific sample may cause an increase in oxidative or other stress levels (e.g. by 20%). In this case, a measurement of stress levels may determine a corrective protocol 106 to restore the samples to their preferred condition. One example of a suitable corrective protocol includes extending the duration of a recovery period, or adding a reagent or substance (e.g., with anti-oxidative properties) to remediate deviation.

This deviation may be detected by periodic (e.g., at a minimum of once per minute) measurement of UV radiation by a spectrophotometer, and when the level deviates from the prescribed by more than a predetermined threshold (e.g., +/−10% or more), for more than 2 minutes or more, the processing circuitry 116 may invoke the corrective protocol.

This deviation may be corrected by first determining the length of time of the deviation measured in seconds and the deviation in UV levels as a fold change. In the case of altered UV levels from prescribed, UV filters, or blinds may be adjusted on in the defined space 104 (or room including the defined space). Living cells 108 may not be removed from the incubator or other enclosure 114, until the UV levels are within what are prescribed.

$O_2$ Deviation, Higher or Lower than Prescribed

In yet another example applicable to a variety of experiments including cellular, chemical and molecular experiments, an elevated oxygen concentration going beyond the prescribed range for a specific sample may cause an increase in oxidative or other stress levels, e.g., by 20%. In this case, a measurement of stress levels may determine a corrective protocol 106 to restore the samples to their preferred condition. One example of a suitable corrective protocol includes extending the duration of a recovery period, or adding a reagent or substance (e.g., with anti-oxidative properties) to remediate the deviation.

This deviation may be detected by periodic (e.g., at a minimum of once per minute) measurement of $O_2$, and when the level deviates from the prescribed by +/−10% or more, for more than 2 minutes or more, the processing circuitry 116 may invoke the corrective protocol.

This deviation may be corrected by first determining the length of time of the deviation measured in seconds and the deviation in environmental $O_2$ as a percentage. In the case of changes in environmental $O_2$, the subject of the experiment may be held in an incubator (enclosure 114) at prescribed $O_2$, for a duration of time determined by the magnitude and duration of the deviation.

Spheroid Size Deviation, Smaller than Prescribed

In yet another example, when working with three dimensional cell culture constructs (e.g., organoids or spheroids or other forms of cell agglomeration), it may be important to conduct experimentation on constructs having reached a certain size (measured as diameter in μm) before starting the experiment. In this case, when constructs are found to deviate from the prescribed by at least a predetermined threshold (e.g., 20% smaller), an empirically-derived corrective protocol 106 may be initiated to account for this deviation. One example includes prolonging the duration of a growth period by 10%, re-examining and repeating the operation as necessary, then resuming the protocol 102 after this specified period of time, allowing the experiment to be conducted under prescribed conditions.

This deviation may be detected from day 4 after seeding, by periodic (e.g., once per 12 hours by automated microscopy) measurement of spheroid diameter in μm in each well of a well plate (container 110). When the mean spheroid size per plate is too small (+/−5% from the specified size), the processing circuitry 116 may invoke the corrective protocol may.

This deviation may be remediated by first determining the diameter of the spheroid via microscopy and by identifying the cell type, and growth kinetics (e.g., determined by prior experiments, or by the observed growth rate for this one sample). And then the subject of the experiment may be held in an incubator at prescribed conditions, for a duration of time determined by the current spheroid size and known/pre-established growth kinetics of the cells.

Fragmentation Size, Larger than Prescribed

In yet another example, in certain experiments involving nucleic acids or other cell components, and which may be a precursor to non-cellular chemical or molecular experiments, it may be important to shear these nucleic acids or other components into small fragments. If the fragments deviate from the prescribed size the experiment may be negatively impacted. In this case, after a first fragmentation operation (which could happen via sonication, enzyme digestion, physical disruption or other means) the size of the fragments may be measured and if they are found to deviate from the prescribed size by at least a predetermined threshold (e.g., 50%), or fall outside a different prescribed range pertaining to the experiment, a corrective protocol 106 may be invoked. In one example corrective protocol, the nucleic acids or other cell components may be returned for further rounds of fragmentation or the conditions of the fragmentation may be altered (by changing the sonication amplification, the enzyme concentration, the intensity of the physical disruption etc.) until the component is of an optimal size for the experiment to continue.

This deviation may be detected by optical, electrophoretic, spectrographic or chromatographic means after the first round of fragmentation. When the components are found to be too large, they may be returned for further rounds of fragmentation under substantially the same or altered conditions of fragmentation.

This deviation may be corrected by first determining the mean and range of fragment sizes using optical assays and/or electrophoresis and/or spectrometry and/or chromatography. And then the subject of the experiment may undergo further rounds of fragmentation, the method and duration of which determined by the measured size of the current fragments and the method used for first fragmentation. For example, if the fragmentation exceeds the prescribed size by 50%, the same fragmentation method may be used for a second fragmentation, using a concentration, or a duration, or an intensity level of the first fragmentation that is a fraction of the exceedance (e.g., ½ of 50), and repeated with smaller fractions until the desired fragmentation is achieved.

Gene Product Depletion, Lower than Prescribed

In yet another example that in particular pertains to chemical and molecular experiments, reducing the quantity of a certain protein (e.g., via a reagent or mix of reagents which could silence the gene or the messenger RNA of the protein in question) can be used to determine the effect of specific genes, messenger RNA or proteins on the cell or in response to other stimuli, such as drugs. Some of these silencing reagents have a long incubation time of 72 hours before the experiment can begin and currently there is no easy way of assessing if the silencing has been efficient until the end of the experiment when more time and consumables have been used and potentially wasted. In this case, an early sample of the cells 108 may be taken (12 to 24 hours) after the addition of silencing reagents, and the successful silencing of at least 50% of the messenger RNA or protein may be quantified. The experiment may then continue only if at last the above successful silencing is achieved or if the silencing can be increased to at least 50% by increasing the concentration or the incubation time of the reagent.

This deviation may be detected by optical, electrophoretic, spectrographic, chromatographic or sequencing means, including, e.g., mass spectrometry, polymerase chain reaction (PCR), and SDS-PAGE/Western blotting.

This deviation may be remediated by first determining the degree of silencing of either messenger RNA or protein, and comparing this with the expected kinetics of silencing known for the gene product and silencing agent used in this specific experiment. And then the cells may undergo either a prolonged incubation period with the silencing reagent, until a repeat measurement indicates sufficient silencing, or the concentration of the silencing reagent may be increased based on the reciprocity of the degree of insufficiency in silencing. For example, if the depletion observed is below 50% at day 1, an additional transfection of silencing reagent may be undertaken, up to 50% of the initial volume used and no more than 100 nM siRNA total concentration (initial+corrective), unless knockdown of this gene is known to be detrimental to cell viability. After addition of additional silencing reagent an extra day may be added to the incubation time before the experimental protocol is continued.

Live Cell Count, Lower than Prescribed

In yet another example, before an experiment can be conducted, it can be important to assure the health and viability of cells 108. Using adherent cells as an example, imaging can be used to determine the number of adherent (viable) and floating (dead) cells, as well as to measure and quantify additional cell features (e.g., cell cycle events such as mitosis, shape and size of organelles). In this case, when imaging reveals a small number of mitotic cells (e.g., deviating by 50% from the prescribed conditions), a corrective protocol 106 may be employed to increase the number of live and mitotic cells before a downstream experiment is being conducted. This may involve changing the growth medium 112 in which the cells are being kept to remove any dead/floating cells and other substances contained in the medium which could negatively impact the surviving cells, and/or prolonging the growth period before the experiment is resumed. (For adherent cells, live cells may adhere to the container, floating dead cells are removed when the nutrient liquid is removed and replaced). In another example, a reagent may be added to the growth medium to increase the number of cells in mitosis by blocking the cell cycle.

This deviation may be detected by optical means employing a microscope or another form of imaging device to determine cell morphology. Dying cells shrink and round up, generally having a smoother shape, however the outer membrane starts to create small, round protrusions or 'blebs.'

This deviation may be corrected by first measuring the total number of live, mitotic, and dead cells utilizing automated microscopy or cell counter, calculating the proportion of live and mitotic as well as dead cells relative to the total cell number, and comparing this with the expected total numbers and proportions known for the cell type. When a deviation of more than twofold is detected in the proportion of live, mitotic or dead cells, a corrective protocol 106 may be invoked. For example, the cells may undergo either a medium change (to remove dead floating cells) or a prolonged incubation period in case of decreased numbers of live or increased numbers of dead cells, until a repeat measurement indicates the prescribed conditions being reached. In case of decreased numbers of mitotic cells, reagent or growth factors may be added to the medium to increase the number of cells in mitosis. At the end of the corrective action, a final medium change can be performed to remove the detritus (debris) of dead cells.

Adherent Cell Count, Lower than Prescribed

In yet another example, cells 108 may need to become adherent to their container 110 before an experiment can be continued. In this case, imaging may be used to quantify the number of adherent cells by measuring their size, shape and position. If more than a predetermined threshold (e.g., 20%) of the cells are found to be non-adherent, a corrective protocol 106 may incrementally increase the incubation time until less than a predetermined percentage (2 to 10%) of cells are found to be non-adherent, before resuming the protocol 102.

This deviation may be detected by optical means employing a microscope or another form of imaging device. The deviation may be corrected by first measuring the total number and calculating the proportion of non-adherent cells to the total cell number, and comparing this with the expected total numbers and proportions known for the cell type. When a deviation of more than twofold is detected in the proportion of adherent cells, a corrective protocol may be invoked. This may include the cells undergoing a prolonged incubation period, with periodic measurement, until a repeat measurement indicates the prescribed conditions being reached at which point the cells can be processed in other downstream applications and protocols.

Confluence of Cells, Higher or Lower than Prescribed

In yet another example, cells 108 must be maintained in a pre-determined, prescribed range of confluence (50-80%) in order to remain in the log phase of their cell growth. If the cells are less confluent they may grow slower than expected and if they are more confluent their gene expression profiles and growth properties may change, and they may start to die. In this case, imaging may be used to monitor and quantify the confluence of the cells in intervals determined by prior experimentation. If the cells are less than a predetermined threshold (e.g., 50%) confluent, the media may be refreshed, whereas cell splitting may occur if the cells are within 50-80% confluence or more.

This deviation may be detected by optical means employing an imaging device such as a microscope. The deviation may be remediated by determining the degree of confluence by periodic (e.g., at a minimum of once per 6 hours) measurement, and when the confluence is less than 50% or within 50-80% or more than 80%, a corrective protocol 106 may be invoked.

In the case of confluence lower than 50%, the cells 108 may undergo a prolonged incubation period, until a periodic repeat measurement indicates that confluence has reached 50-80%, in which case the cells may be deemed suitable for experimental use, and cell splitting may be initiated when either cells are in 50-80% confluence but not required for immediate experimentation, or when they reach more than 80% confluence. If over 80% in confluency, cells may be subcultured to a prescribed culture condition for over 5 days and their growth kinetics analyzed. If their growth kinetics and phenotype recover they can then be used for downstream applications or protocols. If the growth kinetics are different to those observed as prescribed (determined by predetermined experiments) with a greater than, e.g., 20% difference, the cells may be discarded and a new vial may be prepared.

Dead Cell Count, Higher than Prescribed

In yet another example, both before or during an experiment, routine imaging may be performed on containers 110 containing cells 108 to quantify the number of dead cells. If the number of dead cells rises above an experimentally derived threshold, a corrective protocol 106 may be initiated to diagnose and if possible correct for any potential influence explaining the increase in cell death.

In this case, if imaging detects a dead cell count higher than prescribed, a sample may be taken to be tested for the presence of infection (e.g., fungal, bacterial (including mycoplasma), viral). If the test is negative, the media may be replaced and the cells 108 returned to the incubator (enclosure 114) to grow until a follow up check is made 12 to 24 hours later. If the test is positive, the cells must be removed from the incubator and discarded to reduce the chance of other cells becoming infected. A new batch of cells may then be taken from storage and defrosted to resume the protocol 102 with a fresh set of cells.

The number of dead cells may be detected by optical means employing a microscope or another form of imaging device, whereas for the detection of the presence of an infection a sample may be taken with a sterile pipette and analyzed via optical, electrophoretic, spectrographic, chromatographic or sequencing means, including, e.g., mass spectrometry, PCR and dyes specific for bacterial or viral particles.

This deviation may be corrected by determining the number and proportion of dead cells by routine measurement during ongoing experiments and cell culture at least every 12 hours, comparing the proportion of dead cells with the expected total numbers and proportions known for the cell type and experiment. When a deviation of more than twofold is detected in the proportion of dead cells, a sample may be taken and analyzed for presence of infection and a corrective protocol 106 invoked. In the case of the proportion of dead cells deviating more than twofold from the proportion prescribed for the cell type and experiment, a sample may be taken and analyzed for the presence of infection. If no infection is detected, cells 108 may be returned to their experiment or their incubation and both the quantification of the proportion of dead cells and the analysis for the presence of an infection may be repeated after 12 hours. When an infection is detected, the experimental container found to contain infected cells may be discarded and the experiment restarted with a fresh batch of cells.

Dyeing Process, Faster or Slower than Prescribed (in Living Cells)

In yet another example, it may be necessary to add certain dyes to cells 108 or other samples which may then allow a certain analysis to be performed (e.g., taking an image, a fluorescent or luminescent readout etc.). Depending on their type, these dyes or other substances may require a specified duration of time for binding or attachment to a certain cell, part of a cell, or other substance, permission of the cell wall, etc. And dyeing live cells may require the dye to be taken across the cell membrane.

In this case, before taking the final analysis operation—which might be irreversible—a pre-inspection may take place to check for the success of the dyeing process, by taking an initial readout. If, for example, only 70% of the cells or samples have been dyed, a corrective protocol 106 may be initiated to prolong the incubation time by 1 hour and to repeat this operation as necessary.

The success of the dyeing operation may be detected by optical means employing a microscope or another form of imaging device.

This deviation may be corrected by determining the proportion of dyed samples by measurement at 80% of the prescribed incubation time after addition of the dye, quantifying the proportion of dyed cells or samples. When less than 80% of cells or samples have been successfully dyed, a corrective protocol may be invoked. In the case of the proportion of dyed cells or samples being less than 80%, the cells 108 or samples may be subjected to an additional incubation time determined by the product of the proportion of non-dyed cells or samples and the prescribed incubation time. The analysis of the success of the dyeing process may be repeated at, e.g., ⅘ of this additional incubation time, and further as needed.

Disintegration into Single Cells, Slower than Prescribed

In yet another example, cells 108 may be used as single cells, requiring assertion that cell conglomerates have been completely disintegrated into single cells. In this case, the complete separation of cells into single cell suspension may be checked in advance of starting or continuing an experiment, and if only a certain percentage (e.g., 80%) of the cells have been found to have been singled, a corrective protocol 106 may be invoked to either increase the time or the intensity of the disintegration process (by adding a higher amount of enzymes such as trypsin, or increasing the rotations per minute of a grinder or frequency of a syringe movement).

The separation of cells into single cells may be detected by optical means employing a microscope or another form of imaging device.

This deviation may be corrected by determining the proportion of single cells before an experiment starts with single cells. When less than 80% of cells are found to be single cells, a corrective protocol 106 may be invoked. In the case of the proportion of single cells being less than 50-80%, the cells or samples may be subjected to an additional incubation time (with trypsin or in the grinder) determined by the proportion of non-singled cells or, if the proportion of single cells being less than 50%, the cells may be subjected to an intensified disintegration protocol. The analysis of the proportion of single cells may be repeated at, e.g., ⅘ of the additional incubation time, and further as needed.

Health of Cells, Lower than Prescribed—Divide Several Versions

In yet another example, observable features of cells 108 (e.g., their size, shape, surface area, surface markers, content, color—such size/shape/number of organelles, inclusion bodies) may be assessed to draw conclusions on cell health, viability, stress levels, metabolic activity, mitotic activity, and other features. In this case, when a deviation from the expected prescribed parameters is recorded, a corrective protocol 106 to return the cells their prescribed conditions may be invoked. This may include the addition of supplements or removal of harmful substances or reagents, the exchange of the medium used, the splitting of cells and other means. For example, cells showing decreased metabolic activity by 50% may receive fresh medium supplemented with a set of substances to return their metabolic activity to prescribed levels.

The health of cells 108 may be assessed by optical means employing a microscope or another form of imaging device. When signs of abnormal cell health are detected, a sample may be taken with a sterile pipette and an analysis made using optical, electrophoretic, spectrographic, chromatographic or sequencing means, including, e.g., mass spectrometry, PCR and Western blotting, for the quantification of the concentration of nutritional factors, metabolic products, ions, and proteins.

This deviation may be remediated by microscopic imaging and when signs of abnormal cell health are detected in the form of deviations in cell shape, organelle characteristics, presence of inclusion bodies or membrane blebbing, then initiating additional analysis for a detailed assessment of cell health, invoking a corrective protocol 106 directed towards returning the conditions found to deviate from the prescribed conditions. In the case of the health of cells deviating from the prescribed conditions, a detailed assessment quantifies deviations from the prescribed conditions of the components of the medium, leading to the addition of substances lacking, and the removal of substances being in excess, by exchanging the medium with fresh medium of a composition suited to the type of cell in question.

Differentiation of Cells, Fewer than Prescribed Cells Differentiated

In yet another example, cells 108 can display varying degrees of differentiation, and a population may thus include cells which vary between embryonic and fully differentiated. In order to conduct experiments with homogenous cell populations, it can be important to ascertain a common degree of differentiation within a population. In this case, when measuring the degree of differentiation shows a certain percentage (e.g., 10%) of cells to be non- or under-differentiated, a corrective protocol 106 may be employed to first separate the subpopulation of non- or under-differentiated cells, and to then initiate a differentiation process using suitable reagents.

Differentiation may be measured by measuring expression of lineage specific marker proteins through immunofluorescence/flow cytometry analysis, or by cell specific function analysis (the exact measurement may vary according to cell type) such as by measuring action potentials of cardiomyocytes or insulin release of β-islet cells upon glucose addition.

Key parameters here may include the proportion of cells within a population which have undergone differentiation via flow cytometry, cell function analysis or immunofluorescence. A corrective protocol 106 for this deviation may in particular include separating the sub-populations of cells via FACS sorting. Those which remain undifferentiated may be treated with the appropriate substance, or chemical to induce differentiation. Those which are differentiated may be allowed to continue into the downstream experiment, or re-seeded into a flask to be kept in culture until required.

Controlled Freezing/Thawing

In yet another example, the freezing and thawing process of cells 108 or other reagents, including the thawing of reagents stored in a frozen state, needs to be tightly controlled to ensure the integrity of the substances. In this case, the freezing and thawing process may be monitored to ensure it follows a predetermined temperature gradient. When a deviation from the temperature gradient is detected, the temperature of the freezing/thawing container may be altered, and/or the time in the freezing/thawing container may be changed, to return the temperature gradient to its prescribed conditions.

This deviation may be measured by monitoring of temperature of the cells or reagents as it freezes or thaws.

Cells, reagents, or sample may have a predetermined freeze/thaw rate established as prescribed. The rate may be measured continuously during the freeze/thaw process and when the observed rate is deviated from a prescribed rate (e.g., over 10%), a corrective protocol 106 may be triggered. This may include the freezing/thawing container having a temperature adjustment to either speed up, or slow down freeze/thaw as appropriate to bring the rate back into line with prescribed conditions.

Gene Expression changes, Higher or Lower than Prescribed

It is also known that changes in conditions such as pH, light exposure, temperature and the like can influence and alter gene expression levels in cells 108. In this case, after the occurrence of a deviation from the prescribed conditions, cells may be assessed for changes in gene expression, which can then be accounted or corrected for by a corrective protocol 106 such as adding substances altering the gene expression or the gene product quantities in such a way that the prescribed conditions are reached.

Deviations from conditions such as pH, light, planned incubation with substances and temperature may be detected by logging any events which cells 108 undergo. This logging includes recording of the time and duration as well as quantity/intensity of the exposure. Means of detection include thermometer, pH-meter, luxmeter, spectrographic and chromatographic measurements. If the exposure exceeded the threshold for prescribed exposure parameters by twofold, an assessment of gene expression changes may be made employing quantification of messenger RNA and/or proteins via microarrays, RNA-Seq, Western blotting, mass spectrometry or other suitable means.

Temperature may be recorded in ° C., pH in logarithmic units, light intensity in lux, and substances in concentrations of units per ml or μmol. A deviation of more than twofold then leads to a corrective protocol 106 starting with the quantification of changes in gene expression caused by the deviations in the prescribed conditions. Genes found to be upregulated may consecutively be reduced in their expression by adding substances that silence the respective genes (or their transcription/translation, respectively). Genes found to be downregulated may be increased in their expression by adding substances that enhance the respective genes (or their transcription/translation, respectively). The quantities may be determined by sequencing, qRT-PCR and/or SDS-PAGE/Western blotting.

Shear Stress, Higher than Prescribed

In yet another example, cells 108 may be analyzed flowing within a microfluidic device. In this case, when shear stress exceeding the experimentally-determined prescribed conditions is detected, a corrective protocol 106 may reduce the flow rate in a microfluidic device to return the conditions to their prescribed values.

Deviations from the prescribed levels of shear stress may be detected via optical means employing an imaging device (e.g., microscope or another form of imaging device). Shear stress may be quantified in relation to the flow rate/velocity and compared with the prescribed levels of shear stress known for this cell type and flow rate/velocity. If shear stress exceeds the prescribed values by a predetermined percent (e.g., 50%), a corrective protocol 106 may be invoked.

To reduce the shear stress and return it to prescribed levels, the flow rate/velocity in the microfluidic device may be reduced by a percentage in proportion to the deviation in shear stress experienced. The effect of the corrective protocol 106 may be re-assessed periodically once per minute to assure return to prescribed conditions.

Spheroid Analysis, Larger than Prescribed

Measuring spheroid size or volume is an established way of measuring response to treatment with a drug or radiation (shrinkage, disintegration and regrowth) compared to control-treated spheroids (which continue to grow), used to determine the effectiveness of the treatment. Typically spheroids are measured every 3-4 days until they reach a specific predetermined size, or a predetermined time limit is met, e.g., $5\times V_0$ (5 times the volume they were on the day they were initially treated—day 0) for up to 60 days. As microscopy may be used to determine this, there may be a time lag taken to both take photos and automatically analyze volume of each individual spheroid in an experiment. However, once a spheroid has reached $5\times V_0$ there may be no need to continue monitoring growth which would reduce time per plate as the experiment continues.

In this case, the size of each spheroid may be measured by phase contrast, or brightfield microscopy at day 0 and the $5\times V_0$ calculated. On every third day subsequent to treatment the spheroids may be measured. When any one spheroid reaches, or exceeds, its $5\times V_0$ it may be removed from further analysis—measurement of this well (container 110) may automatically be ceased at the day it reaches this value, thereby enabling the plate to be read faster and the analysis to be completed quicker.

This deviation may be detected by measuring the size and volume of spheroids in microplates via automated phase contrast, or brightfield microscopy.

Automated phase contrast or brightfield microscopy may be used to image spheroids in microplates. Automated image analysis may be used to determine spheroid diameter and volume and to calculate $5\times V_0$ from the first measurement. And then software may automatically skip measurement and further analysis of the wells which have already reached, or exceeded $5\times V_0$, but continue measurement of those wells which have not reached this value until they reach $5\times V_0$ or 60 days after treatment.

It should be appreciated that protocols 102 and corrective protocols 106 for biological experiments according to example implementations may be performed manually, with minimal use of automated equipment. Or the same protocols and corrective protocols may be substantially performed by automated equipment as directed by processing circuitry 116. In this light, the protocols and corrective protocols disclosed herein may be performed by humans or by machines, or combinations thereof, without limitation on who or what performs the operations except in cases where the operations require use of a specific device, such as a microscope, or a gas concentration sensor.

Many modifications and other implementations of the disclosure set forth herein will come to mind to one skilled in the art to which this disclosure pertains having the benefit of the teachings presented in the foregoing descriptions and the associated figures. In this regard, although primarily described in the context of cellular experiments, example implementations may be applicable to other types of biological experiments including chemical and molecular experiments. Examples of suitable chemical experiments that involve cell fragments include RNA extraction, DNA extraction, nucleic acid separation by size and Northern and Southern blotting, protein extraction, protein separation by size or charge and Western blotting, nuclear extraction, restriction enzyme digestions and the like. Examples of suitable molecular experiments include PCR (polymerase chain reaction), cloning, DNA ligation and plasmids, ELISA (enzyme-linked immunosorbent assay) and microarrays and ChIP (chromatin immunoprecipitation).

Therefore, it is to be understood that the disclosure is not to be limited to the specific implementations disclosed and that modifications and other implementations are intended to be included within the scope of the appended claims. Moreover, although the foregoing descriptions and the associated figures describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A system for performing a biological experiment, the system comprising:

a computer-readable storage medium including an experiment protocol and corrective protocols, the experiment protocol specifying a sequence of operations and prescribed conditions for carrying out the biological experiment, the corrective protocols specifying operations for remediating deviations of measurements of the prescribed conditions during the biological experiment; and automated equipment comprising processing circuitry, at least one robot and sensors, the processing circuitry coupled to the at least one robot and the sensors;

wherein the processing circuitry is programmed to access the experiment protocol from the computer-readable storage medium;

wherein the processing circuitry is programmed to cause the automated equipment to perform the sequence of operations to carry out the biological experiment according to the experiment protocol, the sequence of operations including the at least one robot dispensing cells into a container containing a growth medium, and the at least one robot transferring the container containing the cells and the growth medium into an enclosure for culturing the cells;

wherein the sensors are configured to measure and thereby produce the measurements of the prescribed conditions, at least some of the prescribed conditions including an incubation period in which the container containing the cells and the growth medium is held in the enclosure, physical and chemical conditions outside or within the enclosure, one or more physical or chemical properties of the cells or the growth medium within the container, or conditions of the cells or cells' concentration within the container; and wherein the processing circuitry is programmed to:

obtain the measurements of the prescribed conditions from the sensors;

compare the measurements of the prescribed conditions to the prescribed conditions;

detect a first deviation of a first measurement of a first prescribed condition by more than a first predetermined threshold for the first prescribed condition;

interrupt the sequence of operations responsive to detection of the first deviation;

access, from the computer-readable storage medium, a first corrective protocol that specifies a first operation for remediating the first deviation of the first measurement of the first prescribed condition to within the first predetermined threshold;

cause the automated equipment to perform the first operation to remediate the first deviation according to the corrective protocol; and resume the sequence of operations.

2. The system of claim 1, wherein the processing circuitry is further programmed to:

detect a second deviation of a second measurement of the first prescribed condition by less than the first predetermined threshold for the first prescribed condition; and cause the automated equipment to continue the biological experiment without interruption of the sequence of operations to remediate the second deviation.

3. The system of claim 1, wherein the processing circuitry is further programmed to:

detect a second deviation of a second measurement of the first prescribed condition by more than a first critical threshold that is greater than the first predetermined threshold for the first prescribed condition; and cause the automated equipment terminate the biological experiment without the biological experiment being completed, and without remediation of the second deviation.

4. The system of claim 1, wherein the processing circuitry is further programmed to:

detect a second deviation of a second measurement of a second prescribed condition by less than a second predetermined threshold for the second prescribed condition; and cause the automated equipment continue the biological experiment without interruption of the sequence of operations to remediate the second deviation.

5. The system of claim 1, wherein the processing circuitry is further programmed to:

detect a second deviation of a second measurement of a second prescribed condition by more than a second critical threshold that is greater than a second predetermined threshold for the second prescribed condition; and cause the automated equipment to terminate the biological experiment without the biological experiment being completed, and without remediation of the second deviation.

6. The system of claim 1, wherein the sensors are configured to measure and thereby produce measurements of the physical and chemical conditions outside or within the enclosure, including temperature, humidity, and concentration of a gas outside or within the enclosure.

7. The system of claim 1, wherein the sensors are configured to measure and thereby produce measurements of the physical and chemical conditions, including visible or ultraviolet light in the enclosure.

8. The system of claim 1, wherein the sensors are configured to measure and thereby produce measurements of the one or more physical or chemical properties of the cells or the growth medium, including temperature or pH of the growth medium.

9. The system of claim 1, wherein the sensors are configured to measure and thereby produce measurements of the one or more physical or chemical properties of the cells or the growth medium, including a rate of freezing or thawing of the cells.

10. The system of claim 1, wherein the sensors are configured to measure and thereby produce measurements of the conditions of the cells or cells' concentration within the container, including an appearance, size or shape of the cells, clusters of the cells or fragments of the cells.

11. The system of claim 1, wherein the sensors are configured to measure and thereby produce measurements of the conditions of the cells or cells' concentration within the container, including a quantified gene activity in the cells.

12. The system of claim 1, wherein the sensors are configured to measure and thereby produce measurements of the conditions of the cells or cells' concentration within the container, including a count of adherent or floating cells, or confluence of the cells.

13. The system of claim 1, wherein the processing circuitry is programmed to cause the automated equipment to perform the sequence of operations further including the at least one robot adding a dye to the cells, and the prescribed conditions include the conditions of the cells or cells' concentration within the container, including a proportion of the cells to which the dye has attached, or an intensity with which the dye has attached to the cells or the proportion of the cells.

14. The apparatus of claim 1, wherein the automated equipment includes a dispenser;

wherein the at least one robot includes a robot with which the dispenser is equipped, and a robot arm; and wherein the processing circuitry is programmed to cause the automated equipment to perform the sequence of operations including the robot of the dispenser dispensing cells into a container containing a growth medium, and the robot arm transferring the container containing the cells and the growth medium from the dispenser into the enclosure for culturing the cells.

15. The apparatus of claim 1, wherein the sensors are configured to measure and thereby produce the measurements of the one or more physical or chemical properties of the cells or the growth medium within the container, or the conditions of the cells or the cells' concentration within the container.

* * * * *